(12) United States Patent
Cherstkov et al.

(10) Patent No.: US 7,301,059 B2
(45) Date of Patent: Nov. 27, 2007

(54) FLUOROSULFATES OF HEXAFLUOROISOBUTYLENE AND ITS HIGHER HOMOLOGS AND THEIR DERIVATIVES

(75) Inventors: Victor Filippovich Cherstkov, Moscow (RU); Nina Ivanova Delyagina, Moscow (RU); Viacheslav A. Petrov, Hockessin, DE (US); Weiming Qiu, Wilmington, DE (US); Paul R. Resnick, Cary, NC (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/726,449

(22) Filed: Mar. 22, 2007

(65) Prior Publication Data

US 2007/0167640 A1    Jul. 19, 2007

Related U.S. Application Data

(62) Division of application No. 10/435,003, filed on May 9, 2003.

(60) Provisional application No. 60/380,528, filed on May 14, 2002.

(51) Int. Cl.
*C07C 19/08* (2006.01)
*C07C 21/18* (2006.01)
*C07C 23/00* (2006.01)

(52) U.S. Cl. ..................... 570/124
(58) Field of Classification Search .......... None
See application file for complete search history.

(56) References Cited

U.S. PATENT DOCUMENTS

| | | | |
|---|---|---|---|
| 2,352,554 A | 6/1944 | England | |
| 3,706,723 A | 12/1972 | Chandrasekaran et al. | |
| 4,131,740 A | 12/1978 | England | |
| 4,235,804 A | 11/1980 | Krespan | |
| 6,140,436 A | 10/2000 | Doyle et al. | |
| 2003/0013816 A1 | 1/2003 | Bekiarian et al. | |

FOREIGN PATENT DOCUMENTS

| | | |
|---|---|---|
| EP | 0 121 073 B1 | 7/1987 |
| EP | 0 728 776 B1 | 10/1998 |
| EP | 1 148 041 A2 | 10/2001 |
| GB | 1 219 063 | 1/1971 |
| WO | WO 00/55130 | 9/2000 |
| WO | WO 01/37043 A1 | 5/2001 |
| WO | WO 02/093261 A1 | 11/2001 |
| WO | WO 2002093261 | * 11/2002 |

OTHER PUBLICATIONS

March, Jerry, Advanced Organic Chemistry, 4th Edition, Wiley, New York, 1992, p. 205.
Petrov, Journal of Organic Chemistry, 1998, 63, pp. 2988-2992.
Knunyant, I. L., Editor, "Encylclopedia of Chemistry", vol. 1, pp. 994-995, Scientific Publishers, Moscow, 1998.
Zefirow, N. S., Editor, "Encyclopedia of Chemistry", vol. 5, pp. 401-402, Scientific Publishers, Moscow, 1999.

* cited by examiner

*Primary Examiner*—Yvonne Eyler
*Assistant Examiner*—Kellette Gale

(57) ABSTRACT

Hexafluoroisobutylene and its higher homologs are easily reacted with $SO_3$ to give fluorosulfates of the formula $CH_2=C(R)CF_2OSO_2F$, wherein R is a linear branched or cyclic fluoroalkyl group comprised of 1 to 10 carbon atoms and may contain ether oxygen. These compounds react under mild conditions with many nucleophiles to give $CH_2=C(R)CF_2X$, where X is derived from the nucleophile. This reaction provides a route to many substituted hexafluoroisobutylenes, which copolymerize easily with other fluoro- and hydrocarbon monomers such as vinylidene fluoride and ethylene.

10 Claims, No Drawings

FLUOROSULFATES OF HEXAFLUOROISOBUTYLENE AND ITS HIGHER HOMOLOGS AND THEIR DERIVATIVES

FIELD OF THE INVENTION

This invention relates to the synthesis of fluoroolefins

BACKGROUND OF THE INVENTION

Hexafluoroisobutylene's utility is shown by the variety of fluoromonomers and hydrocarbon monomers with which it copolymerizes. For example, it copolymerizes with vinylidene fluoride (U.S. Pat. No. 3,706,723), with vinyl fluoride (International Application WO 2001-037043), with ethylene and tetrafluoroethylene or chlorotrifluoroethylene (European Patent No. 0 121 073 B1), with trifluoroethylene (International Application WO 2001-037043), and with tetrafluoroethylene and vinyl acetate (European Patent No. 1 169 399 A2). Its utility as a component of polymers could be increased if means could be found to add substituents to it. For example, if hexafluoroisobutylene could be substituted to provide functional groups such as acids, the monomer could be used in making fluorinated ion-exchange polymers.

SUMMARY OF THE INVENTION

In one embodiment the present invention provides a compound having the formula $CH_2=C(R)CF_2OSO_2F$, wherein R is a linear, branched, or cyclic fluoroalkyl group comprised of 1 to 10 carbon atoms and may contain ether oxygen.

In a second embodiment the present invention provides a compound having the formula $CH_2=C(CF_2OSO_2F)_2$.

In a third embodiment the present invention provides a compound having the formula $CH_2=C(R)CF_2X$, wherein R is a linear, branched, or cyclic fluoroalkyl group comprised of 1 to 10 carbon atoms and may contain ether oxygen, and X is selected from the group consisting of hydride, halides except fluoride, cyanide, alkoxides, fluoroalkoxides, and perfluoroalkoxides such as $OCF_2CF_2SO_2F$, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides, and thiolmercaptides.

In a fourth embodiment the present invention provides a compound having the formula $CH_2=C(CF_2X)CF_2X'$, wherein X and X' are independently selected from the group consisting of hydride, halides except fluoride, cyanide, alkoxides, fluoroalkoxides, and perfluoroalkoxides such as $OCF_2CF_2SO_2F$, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides and thiolmercaptides.

In a fifth embodiment the present invention provides a process comprising contacting $CH_2=C(R)CF_3$ with $SO_3$ in the presence of a Lewis acid, wherein R is a linear, branched, or cyclic fluoroalkyl group comprised of 1 to 10 carbon atoms and may contain ether oxygen, to produce a $CH_2=C(R)CF_3/SO_3$ adduct. A preferred compound of the formula $CH2=C(R)CF_3$ for use in this process is hexafluoroisobutylene (R is $CF_3$).

In a sixth embodiment the present invention provides a process comprising contacting $CH_2=C(R)CF_2OSO_2F$ with a first nucleophile, wherein R is a linear, branched, or cyclic fluoroalkyl group comprised of 1 to 10 carbon atoms and may contain ether oxygen, to produce a substitution product. Preferred nucleophiles are selected from the group consisting of hydride, halides, cyanide, alcohols, alkoxides, fluoroalkoxides, and perfluoroalkoxides such as $^-OCF_2CF_2SO_2F$, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides and thiolmercaptides.

In a seventh embodiment the present invention provides a process comprising contacting $CH_2=C(CF_2OSO_2F)_2$ with a first nucleophile and then with a second nucleophile, different from said first nucleophile to produce a substitution product.

In an eighth embodiment the present invention provides copolymers of $CH_2=C(R)CF_2X$, wherein R is a linear, branched, or cyclic fluoroalkyl group comprised of 1 to 10 carbon atoms and may contain ether oxygen, and X is selected from the group consisting of hydride, halides except fluoride, cyanide, alkoxides, fluoroalkoxides, and perfluoroalkoxides, aryl oxides, fluoroaryloxides, and perfluoroaryloxides such as $OCF_2CF_2SO_2F$, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides, and thiolmercaptides, and at least one other monomer.

In a ninth embodiment the present invention provides a compound having the formula $CF_2=C(R)CH_2X$, wherein R is a linear, branched, or cyclic fluoroalkyl group comprised of 1 to 10 carbon atoms and may contain ether oxygen, and X is selected from the group consisting of hydride, halides except fluoride, cyanide, alkoxides, fluoroalkoxides, and perfluoroalkoxides such as $OCF_2CF_2SO_2F$, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides and thiolmercaptides.

In a tenth embodiment the present invention provides compound having the formula $CF_2=C(CF_2X)CH_2X'$ wherein X and X' are independently selected from the group consisting of hydride, halides except fluoride, cyanide, alkoxides, fluoroalkoxides, and perfluoroalkoxides such as $OCF_2CF_2SO_2F$, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides and thiolmercaptides.

DETAILED DESCRIPTION

Hexafluoroisobutylene has been discovered to react easily with sulfur trioxide ($SO_3$) in the presence of a Lewis acid to yield a hexafluoroisobutylene/$SO_3$ adduct, $CH_2=C(CF_3)CF_2OSO_2F$, referred to herein as hexafluoroisobutylene fluorosulfate or HFIBFS. Suitable Lewis acids include $BF_3$, $B(OCH_3)_3$, $SbF_5$, $SbCl_5$, $BCl_3$, $B(OC(=O)CF_3)_3$, $B(OSO_2CF_3)_3$, $B_2O_3$, $H_3BO_3$, and $Na_2B_4O_7$ (It is recognized that $Na_2B_4O_7$ is not in itself a Lewis acid. However, it behaves like a Lewis acid in the presence of $SO_3$.).

Preferred Lewis acids are $BF_3$, $B(OCH_3)_3$, and $SbF_5$. Reaction temperature is in the range of about −50 to 100° C., preferably about −25 to 75° C., more preferably about 0 to 50° C., still more preferably about 10 to 40° C., and most preferably about 20 to 30° C. With occasional or continuous stirring or agitation, a satisfactory yield of HFIBFS is obtained in about 1 minute and greater, preferably about 1 minute to about 100 hours.

In addition to HFIBFS, the reaction of hexafluoroisobutylene with $SO_3$ can also be made to yield the diadduct, $CH_2$=$C(CF_2OSO_2F)_2$, referred to herein as hexafluoroisobutylene difluorosulfate or HFIBFS2. $CH_2$=$C(CF_2OSO_2F)_2$ is produced by increasing the molar ratio of $SO_3$ to hexafluoroisobutylene to greater than 1. Yields of the difluorosulfate are increased as the $SO_3$ to hexafluoroisobutylene molar ratio is increased. At a molar ratio of greater than 2, difluorosulfate can be expected to be the predominant product.

The reaction with $SO_3$ is not limited to hexafluoroisobutylene, but will take place generally with olefins of the class $CH_2$=$C(CR)CF_3$ to produce a $CH_2$=$C(CR)CF_3/SO_3$ adduct, wherein R is a fluoroalkyl group, preferably a perfluoroalkyl group of from 1 to about 10 carbons, linear, cyclic, or branched. The alkyl group may contain ether oxygen. A member of this class is $CH_2$=$C(C_2F_5)CF_3$. Its reaction with $SO_3$ to give $CH_2$=$C(C_2F_5)CF_2OSO_2F$ is disclosed in the Examples.

The term "fluorosulfate" is used herein to refer to HFIBFS, HFIBFS2, $CH_2$=$C(C_2F_5)CF_2OSO_2F$, and compounds of the general formula above, $CH_2$=$CRCF_2OSO_2F$.

The fluorosulfates described above, HFIBFS, HFIBFS2, and $CH_2$=$CRCF_2OSO_2F$, have been found to react with nucleophiles to yield substitution products, i.e., compounds of the general formula $CH_2$=$C(R)CF_2X$ and $CH_2$=$C(CF_2X)_2$ (from HFIBFS2), where X is the substituent characteristic of the nucleophile. For example, if the nucleophile is the chloride ion, then reaction gives $CH_2$=$C(R)CF_2Cl$. The reaction proceeds under mild conditions, an indication that the fluorosulfate group (—$OSO_2F$) is an effective "leaving group", that is, it is easily displaced by nucleophiles.

Nucleophiles are atoms or groups of atoms that have unbonded, also known as "free", electron pairs. They may be neutral, amines are examples, or anionic, such as halides. Nucleophiles react with susceptible molecules, attacking, for example, saturated carbon atoms, displacing an atom or group of atoms, the nucleophile thereby becoming bonded to the saturated carbon atom. A discussion of nucleophiles can be found in *Advanced Organic Chemistry*, 4$^{th}$ edition, by Jerry March, Wiley, New York, 1992, p. 205.

Among the nucleophiles suitable for reaction with fluorosulfates are the halides, alcohols, for example, methanol, alkoxides, for example methoxide ($CH_3O^-$), fluoroalkoxides, for example $CF_3CH_2O^-$, and perfluoroalkoxides, for example ($CF_3)_2CFO^-$, and $^-OCF_2(CF(CF_3)$—O—$CF_2)_nCF_2SO_2F$ where n=0-5, aryl oxides, fluoroaryloxides, and perfluoroaryloxides, for example $C_6F_5O^-$, mercaptans, fluoromercaptans, perfluoromercaptans, secondary amines which may be fluorinated, and hydrides, such as sodium borohydride and lithium aluminum hydride. It will be recognized by the skilled artisan that perfluoralkoxides are prepared, preferably in situ, from the corresponding perfluoroketones or perfluoroacid fluorides by reaction with fluoride ion, usually from potassium fluoride (KF). For alkoxides derived from alcohols, such as methanol and hexafluoroisopropyl alcohol, it is not necessary that they be converted to their alkali metal salts to be effective in the reaction according to this invention. The alcohol may be used directly, preferably with added tertiary amine to promote reaction. The anionic nucleophiles are of course accompanied by cations, that is they are salts. The cations are preferably alkali metal cations, chosen so that the salt will be reasonably soluble in the reaction medium. Preferred nucleophiles are halides, more preferably chloride, bromide, and iodide; cyanide, alcohols, alkoxides, fluoroalkoxides, perfluoroalkoxides, aryloxide, fluoroaryloxides, and perfluoroaryloxides. Further preferred nucleophiles are substituted alcohols such as ethylene cyanohydrin ($HOCH_2CH_2CN$), glycidol (2,3-epoxypropanol), ethylene halohydrin ($XCH_2CH_2OH$) such as ethylene chlorohydrin, ethylene bromohydrin, and ethylene iodohydrin, which will provide substituted hexafluoroisobutylene with cyano, epoxy, and halogen functionality. These may also be described as cyanoalkoxides, epoxyalkoxides and haloalkoxides, in keeping with the alkoxide terminology used above, and will be understood to include higher alkylene groups, that may be fluorinated, in addition to the two- and three-carbon molecules described above. Similarly carboxylate functionality can be introduced preferably through the esters thereof through use of hydroxy-substituted organic esters, such as the methyl ester of glycolic acid. These are referred to herein as ester alkoxides. The acids may contain fluorine.

Further preferred nucleophiles are glycols (which are designated herein as hydroxyalkoxides, in keeping with the alkoxide terminology used above), and dithiols, referred to herein as thiolmercaptides, for example $HSCH_2CH_2S^-$, to provide thiol functionality.

The various functionalities provided by the above nucleophiles, particularly the epoxy, hydroxy, amino, cyano, and thiol functionalities confer useful properties on polymers incorporating as comonomers one or more compounds in accordance with the invention containing these functionalities. These useful properties include cross-linkability, dye-ability, adhesion to other materials, such as metals and glass and polar polymers such as polyamides and polyesters. Improved adhesion is useful in fluoropolymers in multilayer structures. Often poor adhesion by the fluoropolymer layer to non-fluoropolymer layers necessitates the use of an interlayer or adhesive. Incorporation of a comonomer that confers adhesive properties on the copolymer can obviate the interlayers and adhesives. These functional groups can also be grafting sites for the attachment of small molecules or large molecules, such as polymers, to modify a copolymer that incorporates as comonomers one or more compounds of this invention.

A particularly useful perfluoroalkoxy nucleophile is $^-OCF_2(CF(CF_3)$—O—$CF_2)_nCF_2SO_2F$ where n=0-5, made according to the disclosures of U.S. Pat. No. 3,301, 893. This is prepared from the corresponding carbonyl fluoride, exemplified here for n=0: $F(O)CF_2CF_2SO_2F$ and KF. $^-OCF_2CF_2SO_2F$ reacts with HFIBFS or HFIBFS2 to give $CH_2$=$C(CF_3)OCF_2CF_2SO_2F$ and $CH_2$=$C(OCF_2CF_2SO_2F)_2$, respectively. The fluorosulfonate functionality of these molecules, i.e. the —$SO_2F$, can be hydrolyzed to give the —$SO_3H$ functionality. This strong acid group is an effective catalyst and ion-exchange group. Therefore by polymerization of $CH_2$=$C(CF_3)OCF_2CF_2SO_2F$ with vinylidene fluoride or other appropriate monomers gives a polymer that after hydrolysis, has ion-exchange character, and is suitable for example, in membranes for batteries, fuel cells, and other electrochemical applications. Similarly, copolymerization of $CH_2$=$C(OCF_2CF_2SO_2F)_2$ gives a polymer in which the ion-exchange groups are "paired", giving a bidentate ligand character to the polymer. Such polymers may be expected to show unusual ion-exchange and sequestering characteristics. Hydrolysis of these sulfonyl fluoride containing polymers can be done in aqueous dimethyl sulfoxide (DMSO) with potassium hydroxide (KOH). A typical recipe is 15% water, 60% DMSO, and 15% KOH. One hour at 70-90° C. is sufficient. The polymer is washed free of salts and DMSO. At this point the polymer is in the potassium ion form, that is, it is a polymer containing potassium sulfonate groups. Acid exchange, for example by treating it several times with 1 N aqueous hydrochloric or nitric acid, converts the polymer to the sulfonic acid form. A milder hydrolysis method, preferred for polymers that contain both hydrogen and fluorine on their carbon backbones, uses ammonium carbonate as the base under milder conditions and is disclosed in U.S. Patent Application Publication No. 2003/0013816. For polymers intended for lithium battery use, the lithium salt of the ionomer can be directly made using lithium carbonate as the base as disclosed in U.S. Pat. No. 6,140,436.

A related perfluoroalkoxy nucleophile that can confer ion-exchange properties on polymer and act as a reactive site is —$OCF_2$—$(CF(CF_3)$—O—$CF_2)_n$—$CF_2COOR$, where R is an alkyl group of 1 to 5 carbon atoms, and n=0-6. This is prepared from F(O)C—$(CF(CF_3)$—O—$CF_2)_n$—$CF_2COOR$ and KF. The acid fluorides are prepared as disclosed in U.S. Pat. No. 4,131,740

The reaction of HFIBFS2 with nucleophiles can be tailored to provide mixed substitution. That is, in the resulting molecule $CH_2$=$C(CF_2X)_2$, the X groups need not be identical. Such a molecule with nonidentical Xs can be represented as $CH_2$=$C(CF_2X)CF_2X'$. One way to promote mixed substitution is to limit the concentration in the reaction medium of the first nucleophile to no more than equimolar with HFIBFS2, and then, after the reaction is complete, to add the second nucleophile.

Compatible solvents, preferably aprotic polar solvents, are advantageously used as the reaction medium for the reaction of fluorosulfates with nucleophiles. Diglyme (bis (2-methoxyethyl) ether), diethyl ether, tetrahydrofuran, sulfolane, acetonitrile, N,N-dimethylformamide, and N,N-dimethylacetamide are more preferred. Diglyme is most preferred. Protic solvents are generally not preferred unless reaction of solvent with the fluorosulfate can be tolerated or is desired.

Temperature for the reaction of fluorosulfates with nucleophiles is in the range of about −25 to 100° C., preferably about 0 to 50° C., more preferably about 15 to 30° C., and most preferably about 20 to 30° C.

In addition to the reaction products having methylene, i.e. $CH_2$=, functionality, isomers are formed also having difluoromethylene functionality. For example, reaction of HFIBFS with chloride ion gives $CH_2$=$C(CF_3)CF_2Cl$ (the methylene isomer) and also $CF_2$=$C(CF_3)CH_2Cl$ (the difluoromethylene isomer). The ratio of the methylene isomer to the difluoromethylene isomer is affected by reaction conditions. In the reaction of HFIBFS with chloride ion, longer reaction time increases the yield of $CH_2$=$C(CF_3)CF_2Cl$ and decreases the yield of $CF_2$=$C(CF_3)CH_2Cl$, as is shown in Example 17. For the purposes of polymerization, the methylene isomer is more desirable.

Compounds described herein, CH2=C(R)CF2X and CH2=C(CF2X)CF2X', where X and X' are the same or different and represent the substituents disclosed above, are suitable for polymerization. Particularly suited are the compounds in which X and X' are selected from the group hydride, halides except fluoride, alkoxides, fluoroalkoxides, and perfluoroalkoxides such as $OCF_2CF_2SO_2F$, mercaptides, fluoromercaptides, perfluoromercaptides, secondary amines which may be fluorinated, azide, hydroxyalkoxides, haloalkoxides, preferably chloroalkoxides, ester alkoxides.

As noted in the Background, experience shows that hexafluoroisobutylene copolymerizes with many monomers, both fluoromonomers, defined herein as monomers having at least one fluorine atom bonded to a doubly bonded carbon atom, and olefinic hydrocarbon monomers. These monomers are suitable for making copolymers in accordance in accordance with the invention and include vinyl fluoride, vinylidene fluoride, ethylene, propylene, vinyl acetate, perfluoroalkyl ethylenes of the formula $CH_2$=$CH$—$C_nF_{2n+1}$ where n=1-10, tetrafluoroethylene, trifluoroethylene, hexafluoropropylene, chlorotrifluoroethylene, fluoro- and perfluoromonomers of the dioxole type, such as 4,5-difluoro-2,2-bis(trifluoromethyl)-1,3-dioxole, perfluoro(alkyl vinyl ethers) such as perfluoro(propyl vinyl ether), perfluoro (ethyl vinyl ether), and perfluoro(methyl vinyl ether). Preferred comonomers are vinyl fluoride, vinylidene fluoride, ethylene, propylene, vinyl acetate, and trifluoroethylene. Copolymers are defined herein as polymers resulting from the polymerization of two or more monomers.

The copolymers in accordance with this invention may be crystalline, i.e. have a melting point as measured by differential scanning calorimetry (DSC), or may be amorphous. Amorphous polymers have utility as components of solutions of polymer, suitable for coatings and articles having good transparency. Amorphous polymers having low glass transitions temperatures (Tg) are useful as elastomers, preferably with Tg below about 20° C., more preferably below about 0° C., most preferably below about −25° C. Compounds in accordance with this invention include monomers with functionality suitable for crosslinking of the kind often used in elastomer technology.

Copolymers of two of the compounds of this invention with vinylidene fluoride are described in the Examples.

EXAMPLES

Hexafluoroisobutylene preparation is disclosed in U.S. Pat. No. 3,894,097. Preparation of $CH_2$=$C(CF_3)C_2F_5$ (3-trifluoromethyl-1,1,1,2,2-pentafluoro-4-butene) is disclosed in the unexamined Japanese patent application (Kokai) 09077700. U.S. Pat. No. 2,852,554 discloses the preparation of $FSO_2CF_2COF$. H-Galden® ZT 85, a trademark of Ausimont, is $HCF_2O(CF_2O)_n(CF_2CF_2O)_mCF_2H$. DP initiator is hexafluoropropyleneoxide dimer peroxide:
$CF_3CF_2CF_2OCF(CF_3)(C=O)OO(C=O)CF(CF_3)$
$OCF_2CF_2CF_3$. Vertrel® XF, a product of E. I. du Pont de Nemours & Co., Wilmington Del. USA, is $CF_3CFHCFHCF_2CF_3$.

Analyses of the products of the examples is done using nuclear magnetic resonance (NMR) both proton NMR ($^1H$) and fluorine NMR ($^{19}F$) and mass spectrometry (MS). Except where noted, NMR analysis is done using an external standard of trifluoroacetic acid or of fluorotrichloromethane ($CFCl_3$, F-11). In the MS results "M" represents the parent molecule. If no solvent is mentioned, the analysis was done on neat material.

Example 1

Preparation of Hexafluoroisobutylene Fluorosulfate ($CH_2$=$C(CF_3)CF_2OSO_2F$) Using $BF_3$ Hexafluoroisobutylene (60 g, 0.36 mole) and $SO_3$ (14 ml, 0.33 mole) that contains about 0.05% $BF_3$ are loaded into a steel autoclave. The autoclave is closed, warmed to 18° C., and shaken for 40 hours. Then the autoclave is chilled, opened, and the contents washed with 30 ml of cold (−10° C.) concentrated sulfuric acid ($H_2SO_4$). The organic layer is separated and distilled to give hexafluoroisobutylene (15 g) and $CH_2$=$C(CF_3)CF_2OSO_2F$ (57.5 g, 85% yield, boiling point (b.pt.) 104-106° C. The conversion is 75%.

$^1$H NMR: δ 5.77 (br.s). $^{19}$F NMR δ −125 (t, ($FSO_2O$); −11.5 (t, ($CF_3$); J($FO_2SO$—$CF_2$)=7 Hz, J($CF_3$—$CF_2$)=7 Hz. MS (m/z, species, intensity %): 225 [M−F]$^+$ (<1); 161 [M−$SO_2F$]$^+$ (12); 145 [M−$OSO_2F$]$^+$ (100); 95 [M−$C_3F_3H$]$^+$ (16); 69 [$CF_3$]$^+$ (20).

Example 2

Preparation of Hexafluoroisobutylene Fluorosulfate $CH_2$=$C(CF_3)CF_2OSO_2F$ Using $SbF_5$ Sulfur trioxide containing 1 wt % $SbF_5$ is charged to a 50 ml steel tube. The tube is then cooled to −70° C., a vacuum applied, and then hexafluoroisobutylene (32.8 g, 0.2 mole) is added. The tube is kept at 20° C. for 48 hours with periodical shaking, after which is cooled to −70° C. and opened. The reaction mixture is washed with cold (−30° C.) concentrated $H_2SO_4$ and then warmed to 25° C. Hexafluoroisobutylene (14 g) is collected in a cold trap. The residue (15.7 g) is $CH_2$=$C(CF_3)CF_2OSO_2F$ (70% yield) and a mixture of pyrosulfates of the general formula $CH_2$=$C(CF_3)CF_2(OSO_2)_nOSO_2F$, where n=1, 2, and 3. The bisfluorosulfate $CH_2$=$C(CF_2OSO_2F)_2$ is not detected. This example demonstrates the utility of $SbF_5$ as a catalyst for the reaction.

Example 3

Preparation of Hexafluoroisobutylene Fluorosulfate $CH_2$=$C(CF_3)CF_2OSO_2F$ Using $B(OMe)_3$ An autoclave is charged with $SO_3$ (28 ml), 0.3 g. trimethylborate ($B(OMe)_3$) and hexafluoroisobutene (130 g, 0.79 mole) The mixture is shaken at ambient temperature for 40 hours. The products from four such reactions are combined and distilled to give hexafluoroisobutene (49 g), a mixture of hexafluoroisobutene and $CH_2$=$C(CF_3)CF_2OSO_2F$ boiling below 97° C. (60 g), and $CH_2$=$C(CF_3)CF_2OSO_2F$ (451.4 g, 64%), b.pt. 98-108° C. This example demonstrates the utility of $B(OMe)_3$ as a catalyst for the reaction.

Example 4

Preparation of Hexafluoroisobutylene Difluorosulfate $CH_2$=$C(CF_2OSO_2F)_2$ Using $BF_3$ Hexafluoroisobutylene (96 g, 0.59 mole) and $SO_3$ (76 g, 0.95 mole) that contains abut 0.5% $BF_3$ are charged to a steel autoclave and stirred at 18-20° C. for 72 hours. The autoclave is then cooled to −70° C. and opened. The reaction mixture is washed with cold (−20° C.) concentrated $H_2SO_4$. The reaction mixture is then distilled, giving hexafluoroisobutylene (13.9 g); $CH_2$=$C(CF_3)CF_2OSO_2F$ (65.8 g, 53.7%); $CH_2$=$C(CF_2OSO_2F)_2$ (40.6 g, 25%), b.pt. 71-73° C. at 15 mm Hg. This example shows that increasing the molar ratio of $SO_3$ to hexafluoroisobutylene to >1 results in production of difluorosulfate. To increase the amount of difluorosulfate, the $SO_3$ to hexafluoroisobutylene ratio need only be increased more. At a molar ratio of >2, difluorosulfate can be expected to be the predominant product.

$^1$H NMR of the difuorosulfate: δ 6.6 (s, $CH_2$). $^{19}$F NMR δ −126.7 (m, ($OSO_2F$); −8.6 (m, ($CF_2$). MS (m/z, species, intensity %): 225 [M−$OSO_2F$]$^+$ (49.9); 145 [$CH_2$=$C(CF_3)CF_2$]$^+$ (95.2); 123 [$C_4H_2H_3O$]$^+$ (100); 141 [$C_4HF_4O$]$^+$ (40.5); 95 [$C_3H_2F_3$]$^+$ (29.5); 83 [$SO_2F$]$^+$ (88.5); 76 [$C_3H_2F_2$]$^+$ (40); 75 [$C_3HF_2$]$^+$ (56.2); 69 [$CF_3$]$^+$ (25.3).

Example 5

Preparation of the Fluorosulfate of $CH_2$=$C(CF_3)C_2F_5$ (3-trifluoromethyl-1,1,1,2,2-pentafluoro-4-butene) Using $B(OMe)_3$ 3-Trifluoromethyl-1,1,1,2,2-pentafluoro-4-butene ($CH_2$=$C(CF_3)C_2F_5$) (10 g, 46 mmoles), $SO_3$ (3.6 g, 46 mmoles, and $B(OMe)_3$ (1 drop) are placed in a glass tube. The tube is sealed at maintained at 18-21° C. for 7 days with periodic shaking. Then the tube is cooled to −70° C. and opened. The reaction mixture is washed with cold (−30° C.) concentrated $H_2SO_4$ and distilled. 3-Trifluoromethyl-1,1,1,2,2-pentafluoro-4-butene (2 g) is recovered and $CH_2$=$C(C_2F_5)CF_2OSO_2F$ (8 g), b.pt. 137° C. Yield is 59%. This example shows that the fluorosulfonation reaction is not limited to hexafluoroisobutylene, but is effective with a higher homologue of hexafluoroisobutylene.

F NMR: δ −126 (t, 1 $^4$F); −12 (m, 2 $^3$F); 8 (m, 3 $^1$F); 38 (m, 2 $^2$F). The superscripts preceding the "F"s identify the fluorine atoms on the molecule:

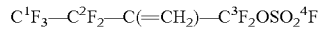

Example 6

Reaction of $CH_2$=$C(CF_3)CF_2OSO_2F$ with $(CF_3)_2CFO^-$ $CH_2$=$C(CF_3)CF_2OSO_2F$ (10 g, 0.041 mole) is added at 20° C. to $(CF_3)_2CFOK$, prepared from freshly dried potassium fluoride (KF) (2.4 g, 0.041 mole), hexafluoroacetone (HFA) (9.3 g, 0.056 mole) and dry diglyme (10 ml). The reaction mixture is agitated for 2 hours and then poured into water, the organic layer separating. The organic layer is washed with dilute hydrochloric acid, then sodium bicarbonate solution, then water, after which it is dried over magnesium sulfate ($MgSO_4$). Distillation of the reaction mixture gives $CH_2$=$C(CF_3)CF_2OCF(CF_3)_2$ (10.2 g, 75% yield, b.pt. 87-88° C.).

Elemental analysis: Found: C, 25.35%; H, 0.60%; F, 69.36%. Calculated: C, 25.45%; H, 0.60%; F, 69.09%. $^1$H NMR (ppm): δ 5.48. $^{19}$F NMR (ppm): δ −11 ($CF_3$); −10 ($CF_2$); 5 ($CF_3$)$_2$; 69.5 ($CF$)$_2$. MS (m/z, species, intensity %): 311 [M−F]$^+$ (5.5); [M−$CF_3$]$^+$ (2.1); 169 [$CF(CF_3)_2$]$^+$ (10.8); 145 [$CH_2$=$C(CF_3)CF_2$]$^+$ (100); 123 ]$CH_2$=$C(CF_3)CO$]$^+$ (90); 69 [$CF_3$]$^+$ (100).

Example 7

Reaction of $CH_2$=$C(CF_3)CF_2OSO_2F$ with $(CF_3)_2CFO^-$

A 250 ml flask is charged with KF (12 g) and diglyme (55 ml) in a dry box. HFA (40.5 g) is added to the mixture via a dry-ice condenser. The solid dissolves completely. $CH_2$=$C(CF_3)CF_2OSO_2F$ (49 g) is added dropwise. The resulting mixture is stirred at room temperature for 3 hours. The mixture is then distilled, yielding a liquid, which is redistilled (spinning band column) to give 36.3 g of $CH_2$=C ($CF_3$)$CF_2$OCF($CF_3$)$_2$, b.pt. 84-86° C., a yield of 55%. Less pure fractions are not included in the yield calculation.

$^{19}$F NMR in with an external $CFCl_3$ standard: δ −65.3 (t, J=8 Hz, 3F); −66.6 (m, 2F); −81.0 (m, 6F); −146.4 (t, J=23 Hz, 1F) ppm. $^1$H NMR δ 6.39 (m) ppm. $^{13}$C NMR δ 101.5 (d & septet, J=269, 38 Hz); 117.1 (qd, J=258, 32 Hz); 118.6 (t, J=274 Hz); 127.4 (m); 131.2 (m) ppm.

Example 8

Reaction of $CH_2$=C($CF_3$)$CF_2$O$SO_2$F with Hexafluoroisopropanol

A 100 ml flask is charged with tributylamine (15 g), diglyme (15 ml), and hexafluoroisopropanol (13.7 g) in a dry box. $CH_2$=C($CF_3$)$CF_2$O$SO_2$F (20.0 g) is added dropwise at 3-12° C. The resulting mixture is stirred at room temperature for 2 hours. The mixture is then distilled to give a liquid, which is redistilled (spinning band column) giving 21.1 g or product, b.pt. 92-93° C. for a yield of 83%. Less pure fractions are not included in the yield calculation.

$^{19}$F NMR in deuterochloroform with an external $CFCl_3$ standard: δ −65.3 (t, J=7 Hz, 2F); −70.8 (m, 2F); −74.0 (q, J=5 Hz, 6F) ppm. $^1$H NMR in deuterochloroform: δ 4.99 (septet, J=5 Hz, 1 H); 6.37 (m, 2H). $^{13}$C NMR in deuterochloroform: δ 69.4 (septet, t, J=35, 4 Hz); 118.8 (t, J=269 Hz); 120.2 (q, J=283 Hz); 120.6 (sextet, J=5 Hz); 130.9 (sextet, J=35 Hz) ppm.

Example 9

Reaction of $CH_2$=C($CF_3$)$CF_2$O$SO_2$F with Trifluoroacetyl Fluoride

Trifluoroacetyl fluoride (6 g, 0.051 mole) is bubbled into a mixture of KF (2.4 g, 0.041 mole) and dry diglyme (15 ml). The reaction mixture is stirred at 20° C. for 30 minutes and then $CH_2$=C($CF_3$)$CF_2$O$SO_2$F (10 g, 0.041 mile) is added gradually. The resulting mixture is stirred at 20° C. for 1 hour. Hexafluoroisobutylene is distilled from the reaction mixture and the residue is poured into water. The organic layer. is separated, washed in turn with aqueous sodium bicarbonate solution and water, and then dried over $MgSO_4$. Distillation gives 3,3-Difluoro-3-pentafluoroethoxy-2-trifluoromethylpropene ($CH_2$=C($CF_3$)$CF_2$OCF$_2$CF$_3$) (3.5 g, 31% yield, b.pt. 67° C.).

$^1$H NMR δ 5.65 (br.s, $CH_2$). $^{19}$F NMR δ −11 (t, 3 $^1$F); −8.1 (tt, 2 $^2$F); J($^1$F—$^2$F)=13 Hz; J($^3$F—$^3$F)=7 Hz. MS (m/z, species, intensity %): 280 [M]$^+$ (5); 261 [M-F]$^+$ (15); 211 [M-$CF_3$]$^+$ (90); 145 [M-$C_2F_5$O]$^+$(95); [$CH_2$=$CCF_3$]$^+$ (80); 69 [$CF_3$]$^+$ (100).

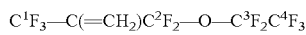

Example 10

Reaction of $CH_2$=C($CF_3$)$CF_2$O$SO_2$F with Trifluoroethanol

A 100 ml flask is charged with tributylamine (15 g), diglyme (20 ml) in a dry box. 2,2,2-Trifluoroethanol (8.05 g) is added to the mixture. $CH_2$=C($CF_3$)$CF_2$O$SO_2$F (19.5 g) is added dropwise while the mixture is cooled in an ice-water bath. The resulting mixture is stirred at room temperature for 3 hours. The mixture is then distilled to give a liquid, which is redistilled (spinning band column) giving 5.8 g $CH_2$=C($CF_3$)$CF_2$OCH$_2$CF$_3$, b.pt. 85-86° C., a yield of 30%. Less pure fractions are not included in the yield calculation.

$^{19}$F NMR (CDCl$_3$); δ −65.4 (t, J=6 Hz, 3F); −72.7 (m, 2F); −75.0 (t, J=8 Hz, 3 F) ppm. $^1$H NMR (CDCl$_3$): δ 4.30 (q, J=6 Hz, 2 H); 6.25 (m, 1 H); 6.28 (m, 1 H) ppm. $^{13}$C NMR (CDCl$_3$): δ 60.9 (qt, J=38, 6 Hz); 118.9 (t, J=264 Hz), 121.4 (q, J=264 Hz); 122.5 (q, J=277 Hz); 126.7 (hex, J=5 Hz); 131.5 (hex, J=33 Hz) ppm.

Example 11

Reaction of $CH_2$=C($CF_3$)$CF_2$O$SO_2$F with 1,1-Dihydroperfluoropropanol

A 100 ml flask is charged with tributylamine (15 g) and diglyme (20 ml) in a dry box. 1,1,-Dihydroperfluoropropanol (24.0 g) is added. $CH_2$=C($CF_3$)$CF_2$O$SO_2$F (19.5 g) is added dropwise at 0-5° C. The resulting mixture is stirred at room temperature for 3 hours. The mixture is then distilled to give a liquid, which is redistilled (spinning band column) giving 27.3 g $CH_2$=C($CF_3$)$CF_2$OCH$_2$CF$_2$CF$_3$, b.pt. 54° C. at 200 mm Hg. Yield is 58%. Less pure fractions are not included in the yield calculation.

$^{19}$F NMR (CDCl$_3$): δ −65.4 (t, J=6 Hz, 3 F); −73.1 (m, 2 F); −84.2 (s, 3 F); −124.3 (t, J=11 Hz, 2 F) ppm. $^1$H NMR (CDCl$_3$): δ 4.40 (tq, J=12 Hz, 2 H); 6.27 (m, 1 H); 6.29 (m, 1 H) ppm. $^{13}$C NMR (CDCl$_3$): δ 59.9 (tt, J=29, 6 Hz); 111.6 (tq, J=264, 38 Hz); 118.3 (qt, J=286, 35 Hz); 118.8 (t, J=265 Hz); 120.6 (q, J=273 Hz); 126.7 (hex, J=5 Hz); 131.5 (6, J=33 Hz) ppm.

Example 12

Reaction of $CH_2$=C($CF_2CF_3$)$CF_2$O$SO_2$F with ($CF_3$)$_2$CFO$^-$ $CH_2$=C($CF_2CF_3$)$CF_2$O$SO_2$F (5 g, 17 mmole) is added at 20° C. to ($CF_3$)$_2$CCFOK, prepared at 10° C. from freshly dried KF (3 g, 17.2 mmole), hexafluoroacetone (HFA) (3 g, 18 mmole) and dry diglyme (15 ml). The reaction mixture is agitated for 1 hour at 20° C. and then poured into water, the organic layer separating. The organic layer is washed with aqueous sodium bicarbonate solution, then water, after which it is dried over (MgSO$_4$). Distillation of the reaction mixture gives $CH_2$=C($CF_2CF_3$)$CF_2$OCF($CF_3$)$_2$ (4 g, 62% yield, b.pt. 118-120° C.). This example demonstrates that the fluorosulfates of the higher homolog of hexafluoroisobutylene react with nucleophiles under the same mild conditions that characterize the reactions of $CH_2$=C($CF_3$)$CF_2$O$SO_2$F.

$^{19}$F NMR δ −8 (tth, 2 $^3$F); 7.9 (m, 3 $^1$F); 38.2 (m, 2 $^2$F); 5 (dt, 6 F); 70 (th, 1 $^4$F); J($^3$F—$^3$F)=33 Hz, J($^3$F—$^5$F)=8 Hz. The superscripts that precede "F" identify the specific fluorine atoms on the compound, as shown in the following structure:

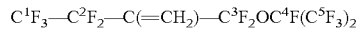

Example 13

Reaction of $CH_2$=C($CF_3$)$CF_2$O$SO_2$F with Methanol

Triethylamine (2.5 g, 0.02 mole) is added gradually to $CH_2$=C($CF_3$)$CF_2$O$SO_2$F (5 g, 0.02 mole) in dry methanol (10 ml) at 10° C. After 20 minutes the reaction mixture is poured into water. The organic layer is separated, washed in turn in dilute aqueous HCl, water, sodium bicarbonate solution, and water, and then dried over $MgSO_4$. Distillation of the dried mixture gives 3,3-difluoro-3-methoxy-2-trifluoromethylpropene (1.8 g, 50% yield). The isomer 1,1-difluoro-2-trifluoromethyl-3-methoxypropene (about 1%) and $CH_2=C(CF_3)COOCH_3$ (about 3%) are also detected by gas chromatography-mass spectrometry (GC-MS).

3,3-difluoro-3-methoxy-2-trifluoromethylpropene: $^1H$ NMR δ 3.1 (s, $CH_3$); 5.6 (s, CH) 5.7 (s, CH). $^{19}F$ NMR δ −11.8 (t, $CF_3$); −2.45 (q, $CF_2$); $J(CF_3-CF_3)=7$ Hz. MS (m/z, species, intensity %): 176 $[M]^+$ (100); 145 $[M-OCH_3]^+$ (75); 95 $[CH_2=C(CF_3)]^+$ (30); 81 $[CF_2OCH_3]^+$ (90); 69 $[CF_3]^+$ (30).

1,1-difluoro-2-trifluoromethyl-3-methoxypropene: MS (m/z, species, intensity %): 176 $[M]^+$ (100); 145 $[CF_2=C(CF_3)CH_2]^+$ (90); 107 $[M-CF_3]^+$ (60); 45 $[CH_3OCH_2]^+$ (90); 69 $[CF_3]^+$ (30).

$CH_2=C(CF_3)COOCH_3$: MS (m/z, species, intensity %): 153 $[M-H]^+$ (5); 123 $[M-OCH_3]^+$ (100); 95 $[CH_2C(CF_3)]^+$ (30); 69 $[CF_3]^+$ (40); 59 $[COOCH_3]^+$ (10).

Example 14

Reaction of $CH_2=C(CF_3)CF_2OSO_2F$ with Pentafluorophenol

Pentafluorophenol (7.5 g, 0.040 mole) and triethylamine (4.5 g, 0.044 mole) in dry ethyl ether (7 ml) are added gradually to $CH_2=C(CF_3)CF_2OSO_2F$ (11 g, 0.045 mole) in ethyl ether (14 ml) at 20° C. The reaction mixture is agitated at 20° C. for 30 minutes and washed in turn with water, dilute aqueous HCl, water, sodium bicarbonate solution, and water and the resulting ether solution is dried over $MgSO_4$. Distillation of the dried mixture gives $CH_2=C(CF_3)CF_2OC_6F_5$ (9.8 g, 73% yield, b.pt. 86-88° C. at 20 mm Hg).

Elemental analysis: Found: C, 36.75%; H, 0.71%; F, 57.06%. Calculated: C, 36.58%; H, 0.61%; F, 57.93%. $^1H$ NMR: δ 5.28 (s), 5.36 (s). $^{19}F$ NMR: δ −10.5 ($CF_3$); −6.5 ($CF_2$); 76 (F in ortho position); 81.5 (F in para position); 87.5 (F in meta position). MS (m/z, species, intensity %): 328 $[M]^+$ (16.8); 183 $[C_6F_5O]^+$ (25.6); 167 $[C_6F_5]^+$ (100); 145 $[CH_2=C(CF_3)CF_2]^+$ (90); 95 $[CH_2=C(CF_3)]^+$ (100).

Example 15

Reaction of $CH_2=C(CF_3)CF_2OSO_2F$ with $FSO_2CF_2COF$

Under the conditions of Example 6 $CH_2=C(CF_3)CF_2OCF_2CF_2SO_2F$ (11 g, 78.6% yield, b.pt. 124-125° C.) is obtained from KF (2.4 g, 0.041 mole), fluorosulfonoxydifluoroacetyl fluoride ($FSO_2CF_2COF$) (9 6, 0.05 mole) and $CH_2=C(CF_3)CF_2OSO_2F$ (10 g, 0.041 mole) and diglyme (10 ml).

Elemental analysis: Found C, 20.62%; H, 0.69%; F, 55.28%. Calculated: C, 20.93%; H, 0.58%; F, 55.23%. $^1H$ NMR: δ 6.05 (m). $^{19}F$ NMR (ppm): δ −121 ($SO_2F$); −11.5 ($CF_3$); −9 ($CF_2O$); 6 ($CF_2$); 36.5 ($CF_2S$). MS (m/z, species, intensity %): 344 $[M]^+$ (7.9); 325 $[M-F]^+$ (3.2); 261 $[M-SO_2F]^+$ (2.3); 164 $[C_2F_4SO_2F]^+$ (45); 161 $[CH^2=C(CF_2O]^+$ (15.6); 145 $[CH_2=C(CF_3)CF_2]^+$ (99); 95 $[CH_2=C(CF_3)]^+$ (100); 69 $[CF_3]^+$ (100).

Example 16

Reaction of $CH_2=C(CF_2OSO_2F)_2$ with $FSO_2CF_2COF$ $CH_2=C(CF_2OSO_2F)_2$ is added gradually to $FSO_2CF_2CF_2OK$, which is prepared from freshly dried KF (3.9 g, 0.067 mole) and $FSO_2CF_2COF$ (12 g, 0.067 mole) in dry diglyme (30 ml). The resulting mixture is stirred 3 hours at 20° C. The reaction mixture is poured into water. The organic layer is washed with aqueous sodium bicarbonate, then water, and then dried over $MgSO_4$. Distillation gives $CH_2=C(CF_3)CF_2OSO_2F$ (0.5 g) and $CH_2=C(CF_2OCF_2CF_2SO_2F)_2$ (9 g, 58% yield, b.pt. 95-96° C. at 15 mm Hg).

Elemental analysis: Found: C, 18.32%; H, 0.38%; F, 50.76%. Calculated: C, 18.32%; H, 0.46%; F, 50.81%. $^1H$ NMR: δ 6.68 (s). $^{19}F$ NMR ($CCl_4$): δ −122.5 ($2^1F$); −10 ($4^4F$); 5 ($4^2F$); 35 ($4^2F$). MS (m/z, species, intensity %): 534 $[M]^+$ (0.1); 505 $[M-F]^+$ (0.07); 325 $[M-OCF_2CF_2SO_2F]^+$ (22.8); 183 $[CF_2CF_2SO_2F]^+$ (13.43); 145 $[C_2F_3SO_2]^+$ (100); 101 $[C_2F_4H]^+$ (56.5); 100 $[C_2F_4]^+$ (21.2); 83 $[SO_2F]^+$ (1.2); 69 $[CF_3]^+$ (18.7). In the $^{19}F$ NMR analysis the superscripts preceding the "F"s identify the fluorine atoms on the molecule:

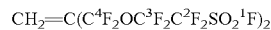

Example 17

Reaction of $CH_2=C(CF_3)CF_2OSO_2F$ with Chloride $CH_2=C(CF_3)CF_2OSO_2F$ (7.9 g, 0.032 mole) is added over 15 minutes to a mixture of dry lithium chloride (LiCl) (1.5 g, 0.036 mole) and dry diglyme (15 ml) at 10° C. with stirring. The reaction mixture is worked up generally as described in other examples and two products, isomers, are identified by GC-MS and $^{19}F$ NMR: 2-Trifluoromethyl-3, 3,-difluoro-3-chloropropene ($CH_2=C(CF_3)CF_2Cl$) (80%) and 1,1-difluoro-2-trifluoromethyl-3-chloropropene ($CF_2=C(CF_3)CH_2Cl$) (14%). The reaction mixture is stirred at 20° C. for an additional 30 minutes. Analysis now shows the amounts of $CH_2=C(CF_3)CF_2Cl$ and $CF_2=C(CF_3)CH_2Cl$ to be present in a ratio of 30:1. The reaction mixture is maintained at 0° C. for an additional 12 hours and now $CH_2=C(CF_3)CF_2Cl$ is the only product found. The reaction mixture is vacuum distilled to separate the $CH_2=C(CF_3)CF_2Cl$, which is then redistilled to give 4.2 g of $CH_2=C(CF_3)CF_2Cl$ (72.4% yield), b.pt. 46-48° C.

This example shows that the ratio of isomers is a function of the reaction time and that the methylene isomer predominates at longer reaction times over the difluoromethylene isomer. This is an indication that the methylene isomer is the more stable isomer at the temperatures used in this example.

$CH_2=C(CF_3)CF_2Cl$: $^1H$ NMR: δ 6.38 (m, and 6.32 m ($CH_2$). $^{19}F$ NMR: δ −24.5 (q, $CF_2Cl$); −12.7 (t, $CF_3$); $J(CF_3-CF_2)=7$ Hz. MS (m/z, species, intensity %): 180 $[M]^+$ (0.2); 161 $[M-F]^+$ (3.4); 145 $[M-Cl]^+$ (100); 119 $[C_2F_5]^+$ (21); 111 $[M-CF_3]^+$ (6.8); 95 $[CH_2CCF_3]^+$ (31); 85 $[CF_2Cl]^+$ (7.8); 75 $[CH=CCF_2]^+$ (20.4); 69 $[CF_3]$ 22.4); 49 $[CH_2Cl]$ (1.2).

$CF_2=C(CF_3)CH_2Cl$: $^1H$ NMR: δ 4.58 ($CH_2Cl$). $^{19}F$ NMR: δ −16 (dd, $CF_3$); −4.5 (q, 2F); −0.5 (q, $^1F$); $J(CF_3-1F)=9$ Hz and $J(CF_31F)=19$ Hz. Note: $^1F$ is the vinyl fluorine on the dihydrochloromethyl side of the double bond. $^2F$ is the vinyl fluorine on the trifluoromethyl side of the double bond.

MS (m/z, species, intensity %): 180 [M]$^+$ (6); 161 [M-F]$^+$ (13); 145 [M-Cl]$^+$ (100); 119 [C$_2$F$_5$]$^+$ (3); 111 [M-CF$_3$]$^+$ (8); 95 [CH$_2$=CCF$_3$] (57.6); 85 [CF$_2$Cl]$^+$ (8.6); 76 [CH$_2$CCF$_2$] (25); 75 [CH=CCF$_2$]$^+$ (61); 69 [CF$_3$]$^{30}$ (50); 49 [CH$_2$Cl]+ (8.7).

Example 18

Reaction of CH$_2$=C(CF$_3$)CF$_2$OSO$_2$F with Bromide

CH$_2$=C(CF$_3$)CF$_2$OSO$_2$F (9 g, 0.037 mole) is added gradually to a mixture of dry sodium bromide (NaBr) (4.5 g, 0.044 mole) and dry diglyme (15 ml) at 10° C. with stirring. The reaction mixture is stirred at 20° C. for 20 minutes and then worked up generally as described in other examples and two products, isomers, are identified by GC-MS and $^{19}$F NMR: 2-Trifluoromethyl-3,3,-difluoro-3-bromopropene (CH$_2$=C(CF$_3$)CF$_2$Br) (67%) and 1,1-difluoro-2-trifluoromethyl-3-bromopropene (CF$_2$=C(CF$_3$)CH$_2$Br) (27%). The reaction mixture is vacuum distilled to separate the CH$_2$=C(CF$_3$)CF$_2$Br, which is then redistilled to give 5.5 g of CH$_2$=C(CF$_3$)CF$_2$Cl (69% yield), b.pt. 69-71° C.

As in Example 17, the methylene and difluoromethylene isomers are found and it is to be expected, as in Example 17, that if the reaction is extended, the predominance of the methylene isomer would increase.

CH$_2$=C(CF$_3$)CF$_2$Br: $^1$H NMR: δ 6.38 m and 6.28 m (CH$_2$). $^{19}$F NMR: δ –29.2 (q, CF$_2$Br); –13 (t, CF$_3$); J(CF$_3$—CF$_2$)=7 Hz. MS (m/z, species, intensity %): 205 [M-F]$^+$ (6.9); 155 [M-CF$_3$]1.6); 145 [M-Br]$^+$ (100); 129 [CF$_2$Br]$^+$ (2); 95 [CH$_2$=CCF$_3$]31.3); 93 [CH$_2$Br]29; 79 [Br]$^+$ (2.3); 69 [CF$_2$]$^+$ (24.7). CF$_2$=C(CF$_3$)CH$_2$Br: $^1$H NMR: δ 4.2 m (CH$_2$Br). $^{19}$F NMR: δ –15.9 (dd, CF$_3$: –5.2 (q, 2F); –1.4 (q, 1F); J(CF$_3$—$^1$F)=10 Hz and J(CF$_3$—$^2$F)=19 Hz. Note: $^1$F is the vinyl fluorine on the dihydrobromomethyl side of the double bond. $^2$F is the vinyl fluorine on the trifluoromethyl side of the double bond. MS (m/z, species, intensity %): 226 [M]$^+$ (1); 207 [M-F]$^+$ (4.4); 155 [M-CF$_3$]$^+$ (1.3); 145 [M-Br]$^+$(100); 131 [CF$_2$Br]$^+$ (1); 126 [M-C$_2$F$_2$]$^+$ (4.7); 119 [C$_2$F$_5$]$^+$ (2.7); 95 [C$_3$H$_2$F$_3$]$^+$ (33.9); 81 [Br]$^+$ (2); 75 [C$_3$F$_2$H]$^+$ (23.2); 69 [CF$_2$]$^+$ (20.2).

Example 19

Reaction of CH$_2$=C(CF$_3$)CF$_2$OSO$_2$F with Iodide

CH$_2$=C(CF$_3$)CF$_2$OSO$_2$F (10 g, 0.04 mole) is added gradually to a mixture of dry sodium iodide (NaI) (7 g, 0.047 mole) and dry diglyme (20 ml) at 10° C. with stirring. The reaction mixture is kept overnight and then poured into water. The organic layer is separated, washed with aqueous sodium bicarbonate solution and then with water and then dried over MgSO$_4$. Distillation gives a mixture (6 g, 54%) of 2-trifluoromethyl-3,3,-difluoro-3-iodopropene (CH$_2$=C(CF$_3$)CF$_2$I) (10%) and 1,1-difluoro-2-trifluoromethyl-3-iodopropene (CF$_2$=C(CF$_3$)CH$_2$I) (90%), as shown by GC-MS and $^{19}$F NMR. B.pt. 98-99° C. The difluoromethylene isomer CF$_2$=C(CF$_3$)CH$_2$I predominates in this example. The experience with chloride as nucleophile (Example 17), indicates that reaction conditions, time in the case of Example 17, can be varied to control the ratio of methylene to difluoromethylene isomer. Simple experimentation should identify conditions at which iodide as nucleophile will yield higher amounts of methylene monomer.

CH$_2$=C(CF$_3$)CF$_2$I: $^1$H NMR: δ 3.7 (CH$_2$I). $^{19}$F NMR: δ–15.5 (dd, CF$_3$); –5 (q, $^2$F); –1.9 (q, $^1$F); J(CF$_3$—$^1$F)=9 Hz and J(CF$_3$—$^2$F)=18 Hz. Note: $^1$F and $^2$F identify vinyl fluorines analogous to the identification in Examples 16 and 17. MS (m/z, species, intensity %): 272 [M]$^+$ (12.9); 253 [M-F]$^+$ (4.8); 241 [M-CF]$^+$ (0.05); 221 [M-CHF$_2$]$^+$ (0.9); 203 [M-CF$_3$]$^+$ (0.6); 177 [CF$_2$I]$^+$ (0.8) 145 [M-I]$^+$ (100) 141 [CH$_2$I]$^+$ (1.5); 127 [I] (38); 119 [C$_2$F$_5$]$^+$ (1); 100 [C$_2$F$_4$]$^+$ (1); 69 [CF$_3$]$^+$ (65); 31 [CF]$^+$ (32.7). CF$_2$=C(CF$_3$)CH$_2$I: $^1$H NMR: δ 5.75 m and 5.85 m (CH$_2$). $^{19}$F NMR: δ –34.2 (q, CF$_2$I); –133 (t, CF$_3$); J(CF$_3$—CF$_3$)=7 Hz. MS (m/z, species, intensity %): 272 [M]$^+$ (0.1); 253 [M-F]$^+$ (4.6); 177 [CF$_2$I]$^+$ (1.5); 145 [M-I]$^+$ (100); 141 [CH$_2$I]$^+$ (0.2); 127 [I]$^+$ (22); 119 [C$_2$F$_6$]$^+$ (2.5); 100 C$_2$F$_4$]$^+$ (0.6); 69 [CF$_3$]$^+$ (58); 31 [CF]$^+$ (48).

Example 20

Reaction of CH$_2$=C(CF$_3$)CF$_2$OSO$_2$F with Fluoride

It will be noted that the product in this example is hexafluoroisobutylene, made by the reaction of CH$_2$=C(CF$_3$)CF$_2$OSO$_2$F with the nucleophile fluoride ion. This would not normally be a practical reaction: CH$_2$=C(CF$_3$)CF$_2$OSO$_2$F is made from hexafluoroisobutylene. The reaction is included here to demonstrate how general the synthetic method of this invention is.

CH$_2$=C(CF$_3$)CF$_2$OSO$_2$F (5 g, 0.02 mole) is added to a mixture of KF (1.2 g, 0.02 mole) and dry diglyme (10 ml) and stirred at 20° C. for 4 hours. $^{19}$F NMR analysis shows the reaction mixture to contain 7.7% CH$_2$=C(CF$_3$)$_2$ (hexafluoroisobutylene). More KF (2.4 g) is added and the resulting mixture stirred at 20° C. for 16 hours. The reaction mixture is distilled, giving 2.5 g (73.5%) hexafluoroisobutylene.

Example 21

Reaction of CH$_2$=C(CF$_2$OSO$_2$F)$_2$ with Chloride

CH$_2$=C(CF$_2$OSO$_2$F)$_2$ (9 g, 0.028 mole) is added gradually to a stirred mixture of dry LiCl (2.5 g, 0.059 mole) and dry diglyme (20 ml) at 10° C. Fifteen minutes after addition is complete the reaction mixture contains two isomers, CH$_2$=C(CF$_2$Cl)$_2$ and CF$_2$=C(CH$_2$Cl)CF$_2$Cl in the ratio 79:14 (analysis by GC-MS and $^{19}$F NMR). The reaction mixture is stirred for an additional 30 minutes at 20° C. The isomer ratio (CH$_2$=C(CF$_2$Cl)$_2$ to CF$_2$=C(CH$_2$Cl)CF$_2$Cl) increased to 90:3. The reaction mixture is kept at 20° C. for two additional days and then distilled, giving 4 g (73%) of CH$_2$=C(CF$_2$Cl)$_2$, b.pt. 85-87° C. This example shows that the behavior of the difluorosulfate CH$_2$=C(CF$_2$OSO$_2$F)$_2$ with the chloride ion is similar to that of the fluorosulfate CH$_2$=C(CF$_3$)CF$_2$OSO$_2$F. Longer reaction time promotes formation of the methylene isomer over that of the difluoromethylene isomer.

CH$_2$=C(CF$_2$Cl)$_2$: $^1$H NMR: δ 6.46 br.s (CH$_2$). $^{19}$F NMR: δ –26.5 (s, CF$_2$Cl). MS (m/z, species, intensity %): 196 [M]$^+$ (0.2); 177 [M-F]$^+$ (2.6; 161 [M-Cl]$^+$ (100); 141 [M-HClF]$^+$ (0.4); 126 [M-2Cl]$^+$ (11.4); 111 [M-CF$_2$Cl]$^+$ (23.8); 93 [C$_3$F$_3$]$^+$ (7.3}; 85 [CF$_2$Cl]$^+$ (32.3); –75 [CF$_2$=C=CH]$^+$ (59); 57 [CF=C=CH$_2$]$^+$ (245.4); 49 [CH$_2$Cl]$^+$ (26). CF$_2$=C(CH$_2$Cl)CF$_2$Cl: $^1$H NMR: δ 3.85 br.s (CH$_2$Cl). $^{19}$F NMR: δ –29.5 (dd, CF$_2$Cl); –6.5 (t, $^1$F); –0.4 (t, $^2$F); J(CF$_2$Cl-$^1$F)=34 Hz and J(CF$_2$Cl—$^2$F)=9 Hz. Note: $^1$F. represents the vinyl fluorine cis to the chloromethyl group. $^2$F represents the vinyl fluorine trans to the chloromethyl group. MS (m/z, species, intensity %): 196 [M]$^+$ (2.4); 177 [M-F]$^+$ (1.7); 161 [M-Cl]$^+$ (100); 141 [M-HClF]$^+$ (0.4); 126 [M-Cl]$^+$ (11.4; 111 [M-CF$_2$Cl]$^+$ (23.8); 93 [C$_3$F$_3$]$^+$ (7.2); 85

[CF$_2$Cl]$^+$ (32.3); 75 CF$_2$=C=CH]$^+$ (59); 57 [CF=C=CH$_2$]$^+$ (25.4); 49 [CH$_2$Cl]$^+$ (26).

Example 22

Reaction of CH$_2$=C(CF$_2$OSO$_2$F)$_2$ with Iodide

CH$_2$=C(CF$_2$OSO$_2$F)$_2$ (15 g, 0.046 mole) is added gradually to a stirred mixture of dry NaI (16.5 g, 0.055 mole) and dry sulfolane (20 ml) at 10° C. with stirring. The reaction mixture is stirred at 20° C. for an additional 20 minutes and poured into water. The organic layer is separated, washed with aqueous sodium bicarbonate solution, washed with water, and then dried over MgSO$_4$. Distillation gives CF$_2$=C(CH$_2$I)CF$_2$I (7.9 g, 57%) b.pt. 58-59° C. at 5 mm Hg. Though no methylene isomer, CH$_2$=C(CF$_2$I)CF$_2$I is found under these reaction conditions, experience with chloride as nucleophile (Example 20), indicates that reaction conditions, time in the case of Example 20, can be varied to control the ratio of methylene to difluoromethylene isomer. Simple experimentation should identify conditions at which iodide as nucleophile will yield higher amounts of methylene monomer.

$^1$H NMR: δ 3.2 br.s (CH$_2$I). $^{19}$F NMR: δ −39.9 (dd, CF$_2$I); −9.5 (t, $^2$F); −2.1 (br.s, $^1$F); J(CF$_2$I—$^1$F)=8 Hz and J(CF$_2$I—$^2$F)=23 Hz. Note: $^1$F represents the vinyl fluorine cis to the iodomethyl group. $^2$F represents the vinyl fluorine trans to the iodomethyl group. MS (m/z, species, intensity %): 253 [M-I]$^+$ (83.7); 177 [CF$_2$I]$^+$ (2); 141 [CH$_2$I]$^+$ (1.6); 127[I]$^+$ (31.4); 126 [C$_2$H$_2$F$_4$]$^+$ (63.7); 100 [C$_2$F$_4$]$^+$ (3.4); 75 [C$_3$HF$_2$]$^+$ (100); 69 [CF$_3$]$^+$ (2.3); 31 [CF]$^+$ (48).

Example 23

Reaction of CH$_2$=C(CF$_3$)CF$_2$OSO$_2$F with Cyanide

Sodium cyanide (2.4 g, 0.04 mole) is added gradually to CH$_2$=C(CF$_3$)CF$_2$OSO$_2$F (10 g, 0.04 mole) in dry acetonitrile (15 ml) at 10° C. The reaction mixture is stirred at 15° C. for 4 hours and then poured into water. The organic layer is separated, washed with water, and dried over MgSO$_4$. Distillation gives a mixture of compounds (3.5 g, 50%, b.pt. 120-122° C.): CF$_2$=C(CF$_3$)CH$_2$CN (93%) and NC—CH$_2$CH(CF$_3$)$_2$ (7%). CF$_2$=C(CF$_3$)CH$_2$CN: $^1$H NMR: δ 2.74 dd (CH$_2$). $^{19}$F NMR: δ −15.1 dd (3 $^1$F); −3.8 dtq ($^2$F); J($^1$F—$^2$F)=21.5 Hz; J($^1$F—$^3$F)=12 Hz; J($^3$F—$^2$F)=11.5 Hz; J($^2$F—CH$_2$)=2.5; J($^1$F—CH$_2$)=2.5 Hz. MS (m/z, species, intensity %): 171 [M]]30); 152 [M-F]$^+$ (25); 102 [M-CF$_3$]$^+$ (100); 75 [F$_2$C=C=CH]$^+$ (25); 69 [CF$_3$]$^+$ (40). Note: $^1$F represents the fluorines of the trifluoromethyl group. $^2$F represents the vinyl fluorine that is cis to the trifluoromethyl group. $^3$F represents the vinyl fluorine that is trans to the trifluoromethyl group. Though no methylene isomer, CH$_2$=C(CF$_3$)CF$_2$CN, is found, experience with chloride as nucleophile (Example 17), indicates that reaction conditions, time in the case of Example 17, can be varied to control the ratio of methylene to difluoromethylene isomer. Simple experimentation should identify conditions at which cyanide as nucleophile will yield higher amounts of methylene monomer.

NC—CH$_2$CH(CF$_3$)$_2$ $^1$H NMR: δ 2.39 d (CH$_2$), 4.8 m (CH); J(H—F)=7.5 Hz; J(H—CH$_2$)=5.5 Hz. $^{19}$F NMR: δ −9.1 d (CF$_3$). MS (m/z, species, intensity %): 172 [M-F]$^+$ (30); 122 [M-CF$_3$]$^+$ (100); 102 [M-CF$_3$-HF]$^+$ (50); 77 [F$_2$C=CH—CH$_2$]$^+$ (50) 69 [CF$_3$]$^+$ (90).

Example 24

Polymerization of CH$_2$=C(CF$_3$)CF$_2$OCH(CF$_3$)$_2$ with CF$_2$=CH$_2$

CH$_2$=C(CF$_3$)CF$_2$OCF(CF$_3$)$_2$ is made according the method of Example 8. A 75 ml stainless steel autoclave chilled to <−20° C. is loaded with 11.6 g of CH$_2$=C(CF$_3$)CF$_2$OCH(CF$_3$)$_2$, 10 ml of CF$_3$CH$_2$CF$_2$CH$_3$ solvent, and 10 ml of ~0.17 M DP initiator in CF$_3$CFHCFHCF$_2$CF$_3$. The autoclave is chilled, evacuated and further loaded with ~2 g of vinylidene fluoride (CF$_2$=CH$_2$). The autoclave is shaken overnight at room temperature. The resulting hazy fluid is dried under nitrogen, then under pump vacuum, and finally for 66 hours in a 75° C. vacuum oven, giving 12.9 g of white polymer. Fluorine NMR in hexafluorobenzene finds the polymer composition to be 53.4 mole % vinylidene fluoride and 46.6 mole % CH$_2$=C(CF$_3$)CF$_2$OCH(CF$_3$)$_2$. Inherent viscosity in hexafluorobenzene at 25° C. is 0.116 dL/g. A small sample is purified for DSC measurement by dissolving 0.5 g of polymer in 3 g of H Galden ZT™ 85 solvent [HCF$_2$O(CF$_2$O)$_m$(CF$_2$CF$_2$O)nCF$_2$H], filtering the haze off using a 0.45 μm PTFE syringe filter (Whatman Autovial®), evaporating off excess solvent, and drying in a 75° C. vacuum oven for 16 hours. The Tg is now 47° C. (10° C./min, N$_2$, second heat).

Solution preparation: A hazy solution is made by rolling 2 g of polymer with 18 g of H Galden™ ZT 85 solvent. The haze is removed by filtering first through a bed of chromatographic silica in a 0.45 μm glass fiber microfiber syringe filter (Whatman Autovial™), centrifuging at 15000 rpm, and finally filtering again through a 0.2 μm PTFE syringe filter (Gelman Acrodisc CR). Evaporation of 119.2 mg of this solution on a glass slide gave a clear film weighing 8.5 mg (solution ~7 wt % in solids).

Example 25

Polymerization of CH$_2$=C(CF$_3$)CF$_2$OCF(CF$_3$)$_2$ with CF$_2$=CH$_2$

CH$_2$=C(CF$_3$)CF$_2$OCF(CF$_3$)$_2$ is made according the method of Example 7. A 110 ml stainless steel autoclave chilled to <−20° C. is loaded with 26 g of CH$_2$=C(CF$_3$)CF$_2$OCF(CF$_3$)$_2$, 25 ml of CF$_3$CFHCFHCF$_2$CF$_3$ solvent, and 10 ml of ~0.17 M DP initiator in CF$_3$CFHCFHCF$_2$CF$_3$. The autoclave is chilled, evacuated and further loaded with ~5 g of vinylidene fluoride (CF$_2$=CH$_2$). The autoclave is shaken overnight at room temperature. The resulting viscous fluid is dried under nitrogen, then under pump vacuum, and finally for 88 hours in a 75° C. vacuum oven, giving 26.7 g of white polymer. Fluorine NMR run in hexafluorobenzene finds the polymer composition to be 51 mole % CH$_2$=C(CF$_3$)CF$_2$OCF(CF$_3$)$_2$ and 49 mole % CH$_2$=CF$_2$.

DSC, 10° C./min, N$_2$, 2nd heat, neither Tg nor Tm detected

Inherent Viscosity, hexafluorobenzene, 25° C.: 0.083

Solution preparation: A clear, colorless solution is made by rolling 2 g of polymer with 18 g of H Galden™ ZT 85 solvent and passing through a 0.45 μm glass fiber microfiber syringe filter (Whatman Autovial™).

What is claimed is:

1. A process comprising contacting $CH_2=C(R)CF_2OSO_2F$ with a nucleophile, wherein R is a linear, branched, or cyclic fluoroalkyl group comprised of 1 to 10 carbon atoms and may contain ether oxygen, to produce a substitution product.

2. A process comprising contacting $CH_2=C(CF_2OSO_2F)_2$ with a first nucleophile to produce a substitution product.

3. A process comprising contacting $CH_2=C(CF_2OSO_2F)_2$ with a first nucleophile and then with a second nucleophile, different from said first nucleophile, to produce a substitution product.

4. The process of claim 1 wherein said nucleophile is selected from the group consisting of hydride, halides, cyanide, alcohols, alkoxides, fluoroalkoxides, and perfluoroalkoxides, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides and thiolmercaptides.

5. The process of claim 2 wherein said first nucleophile is selected from the group consisting of hydride, halides, cyanide, alcohols, alkoxides, fluoroalkoxides, and perfluoroalkoxides, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, epoxy alkoxides, cyanoalkoxides, ester alkoxides and thiolmercaptide.

6. The process of claim 3 wherein said first nucleophile and said second nucleophile are selected from the group consisting of hydride, halides, cyanide, alcohols, alkoxides, fluoroalkoxides, and perfluoroalkoxides, aryl oxides, fluoroaryloxides, and perfluoroaryloxides, mercaptides, fluoromercaptides, perfluoromercaptides, secondary amines which may be fluorinated, azide, cyanate, isocyanate, thiocyanate, hydroxyalkoxides, haloalkoxides, epoxy alkoxides, cyanoalkoxides, ester alkoxides and thiolmercaptide.

7. The process of claim 4 wherein said hydride, halides, cyanide, alkoxides, fluoroalkoxides, and perfluoroalkoxides, aryl oxides, fluoroaryloxides, and perfluoroaryloxides, mercaptides, fluoromercaptides, perfluoromercaptides, azide, cyanate, isocyanate, thiocyanate, hydroxyalkoxides, haloalkoxides, epoxy alkoxides, cyanoalkoxides and thiolmercaptides are present as their alkali metal salts.

8. The process of claim 1 wherein said contacting of said $CH_2=C(R)CF_2OSO_2F$ with a nucleophile is carried out in a compatible solvent.

9. The process of claim 8 wherein said solvent comprises at least one aprotic polar solvent.

10. The process of claim 8 wherein said solvent comprises diglyme.

* * * * *